US010368632B2

(12) United States Patent
Beckman

(10) Patent No.: US 10,368,632 B2
(45) Date of Patent: Aug. 6, 2019

(54) SIMULTANEOUS FLOSSING AND BRUSHING DEVICE

(71) Applicant: Christopher V. Beckman, Los Angeles, CA (US)

(72) Inventor: Christopher V. Beckman, Los Angeles, CA (US)

( * ) Notice: Subject to any disclaimer, the term of this patent is extended or adjusted under 35 U.S.C. 154(b) by 212 days.

(21) Appl. No.: 15/603,433

(22) Filed: May 23, 2017

(65) Prior Publication Data

US 2017/0251799 A1    Sep. 7, 2017

Related U.S. Application Data

(63) Continuation-in-part of application No. 14/860,692, filed on Sep. 21, 2015, now Pat. No. 9,655,704, which is a continuation-in-part of application No. 13/570,241, filed on Aug. 8, 2012, now Pat. No. 9,138,304.

(51) Int. Cl.
| | |
|---|---|
| *A46B 9/04* | (2006.01) |
| *A61C 15/00* | (2006.01) |
| *A46B 11/00* | (2006.01) |
| *A46B 15/00* | (2006.01) |
| *A46B 13/04* | (2006.01) |
| *A61C 15/04* | (2006.01) |
| *A61D 5/00* | (2006.01) |
| *A46B 9/00* | (2006.01) |

(52) U.S. Cl.
CPC .......... *A46B 11/0041* (2013.01); *A46B 9/005* (2013.01); *A46B 9/045* (2013.01); *A46B 11/0062* (2013.01); *A46B 13/04* (2013.01); *A46B 15/0004* (2013.01); *A61C 15/046* (2013.01); *A61D 5/00* (2013.01); *A46B 2200/1086* (2013.01)

(58) Field of Classification Search
CPC ..... A61C 15/00; A61C 15/046; A61C 15/047; A61C 15/048; A46B 9/005; A46B 11/0041; A46B 11/0062; A61D 5/00
See application file for complete search history.

(56) References Cited

U.S. PATENT DOCUMENTS

| | | | |
|---|---|---|---|
| 9,084,655 B2 * | 7/2015 | Sahoo | A61C 15/042 |
| 2014/0366903 A1 * | 12/2014 | Chun | A61C 15/046 |
| | | | 132/200 |

* cited by examiner

*Primary Examiner* — Shay Karls

(57) ABSTRACT

A device adapted for brushing and flossing each of a user's teeth simultaneously is disclosed. Many methods and modes for the device's use are also set forth. In some embodiments, the device is custom-fitted to each user, based on molds, impressions or other 3-dimensional imaging techniques, allowing for a more effective, rapid brushing experience. Customized flossing lines, comprising a wide variety of materials and cleansing products, are set forth in exemplary detail. A specialized handle is set forth, configured for maintaining easy access to controls while leaving the device in place in a user's mouth while cleaning, hands-free.

20 Claims, 12 Drawing Sheets

SIMULTANEOUS FLOSSING AND BRUSHING DEVICE

CROSS-REFERENCE TO RELATED APPLICATION

This application is a continuation-in-part of U.S. patent application Ser. No. 14/860,692, filed Sep. 21, 2015, which itself is a continuation-in-part of U.S. application Ser. No. 13/570,241, filed Aug. 8, 2012. The entire contents of each of those applications are hereby incorporated by reference into the present application as if fully set forth herein.

FIELD OF THE INVENTION

The present invention relates to the fields of tooth-cleaning devices and dentifrices.

BACKGROUND

Although the modern toothbrush did not spread throughout Europe until the 1600s, teeth- and gum-cleaning implements have been in use for many centuries, and date to before recorded history. Typically, in the modern era, a toothbrush includes a handle connected to a set of round-ended, flexible bristles, and is used with toothpaste or other dentifrice and water to clean teeth and gums. In the United States, toothpastes usually include a soap for cleaning and a fluoride compound, for its anti-cavity and pro-mineralization properties to protect teeth from decay. Toothpaste is usually not ingested, and may be poisonous to ingest, although "natural ingredients," such as enzymatic and other toothpaste alternatives, have been developed that may be safer for animals to ingest. Although the safety and efficacy of many specific dentifrices may be debated, the overall health and hygiene benefits of brushing teeth with a toothbrush and a dentifrice is widely accepted and is part of the ordinary routine of a vast majority of people in the most developed countries.

Non-human animals are known to resist having their teeth cleaned by toothbrush because they do not understand its benefits and dislike the sensation. Thus, chewable teeth- and gum-cleaning implements, such as rawhide strips, have been provided to animal pets for many years, to assist in cleaning their teeth. Nevertheless, veterinarians typically view such implements as supplementary if anything, and recommend that mammalian pet owners, especially dogs and cats, brush their pet's teeth with a toothbrush as well, to assist in maintaining oral hygiene and preventing tooth decay. Neglected pet teeth, with no regular manual brushing, and even with some traditional chewing implements, can be very expensive to remediate. Veterinarians may charge $700 or more for cleaning neglected pet teeth, and the pet teeth may still not be restored after such procedures.

SUMMARY OF THE INVENTION

New chewing-actuated teeth cleaning techniques are provided. In some aspects of the invention, an implement with bite-actuated tooth cleaning aspects known and branded as a CLEANCHEW™ is provided, which may comprise tooth and gum brushing protrusion and/or bite-guided channel opening pairings or sets, which channel pairings or sets may include features, projections and/or spacers and one-way valves to permit the biting-actuated release of dentifrice from an inner chamber. In further aspects of the invention, internal springs and the tension of surrounding material aid in creating bite actuation. In still other aspects of the invention, movable bite-actuated and/or motor-actuated members conform an elastomeric or flexible outer layer with additional sub-features that aid in teeth and oral cavity cleaning.

In additional aspects of the invention, a device adapted for brushing and flossing each of a user's teeth simultaneously is disclosed. Many methods and modes for the device's use are also set forth. In some embodiments, the device is custom-fitted to each user, based on molds, impressions or other 3-dimensional imaging techniques, allowing for a more effective, rapid brushing experience. Customized flossing lines, comprising a wide variety of materials and cleansing products, are set forth in exemplary detail. A specialized handle is set forth, configured for maintaining easy access to controls while leaving the device in place in a user's mouth while cleaning, hands-free.

In other aspects of the invention, an interstitial fluid, gel or other medium, which may or may not be present in a separate interstitial layer defined by a lining, and which may or may not include a dentifrice and may or may not change its viscosity, hardness and other properties upon contact with air, aids in enabling re-sealing an inner chamber following penetration of the CLEANCHEW. Outside of that interstitial layer, an additional interstitial layer containing a gas, fluid or other agent that hardens or congeals with or causes to harden or congeal, the interstitial fluid, gel or other medium within the interstitial layer, may be included and, preferably, is comprised of chambers, locks or angled channels that maintain coverage, pressure and/or mixing between the fluids, gels or other media of the two interstitial layers at the point of perforation of a mutual wall, despite a perforation of other walls of the layers. This aspect may also be applied to a variety of other related arts, including but not limited to pneumatic and other tires, to aid in remediating fluid leaks from piercing or other deformation of a pneumatic tire structure. For example, in the instance of a tire, a chamber above each possible point of perforation may have a gradual drain in its wall at a point just above the possible point of perforation, allowing the slow dousing of the perforation with the combined-hardening component in the outer interstitial layer. The fluid, gel or other medium in the outer interstitial layer may also have a signal dye to indicate that the tire has been compromised, while maintaining pressure due to the resulting seal from hardening or congealing by mixing of the two layers of fluid, gel or other medium.

Unless otherwise indicated, the following terms have the specific meaning described herein:

A "CLEANCHEW," in addition to its ordinary meaning and special meaning in the art to which it pertains, means each of the following aspects, both alone and in each possible combination, as if separately set forth: an object, preferably comprising an elastomeric or other pliant, flexible or rebounding solid material, that may be chewed and/or bitten by an animal and, due to such chewing and/or biting either or both: (1) releases a fluid, gel, liquid and/or dentifrice from a contained cavity or other feature of the CLEANCHEW in the direction of outer or scrubbing features of the CLEANCHEW or of the teeth or other oral cavity features of the animal; and/or (2) leads to and/or actuates scrubbing or cleaning by protrusions or other features on the outer surface of the object. In addition or alternatively, a CLEANCHEW may comprise a refillable inner chamber(s) variably containing dentifrice and/or any animal-bitable object that may aid in the animal's oral hygiene.

DETAILED DESCRIPTION OF THE INVENTION

Figure 1:
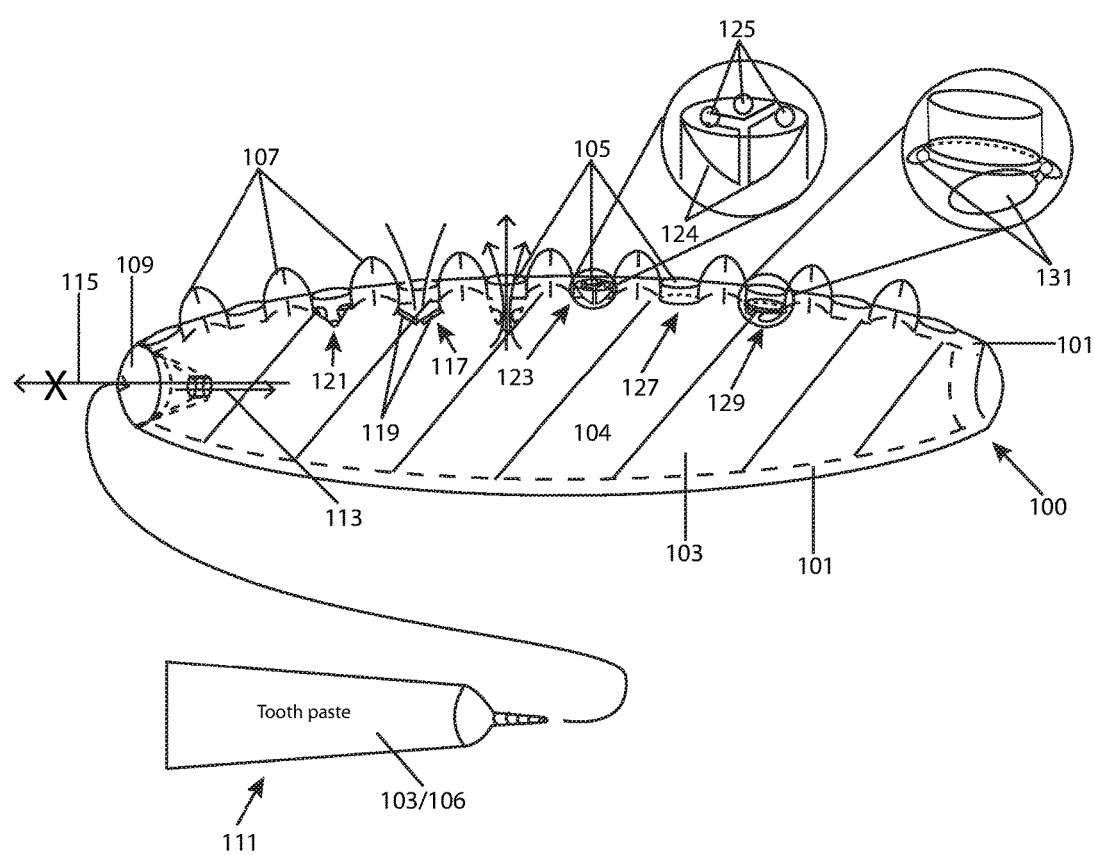
FIG. 1 is a partial illustration of some components of a CLEANCHEW and incorporated dentifrice, in accordance with aspects of the present invention.

FIG. 1 is a side-view illustration of a CLEANCHEW bite-actuated cleaning system 100 for mammalian pets. The entire CLEANCHEW is designed to be safely bitten by a typical mammalian pet, and preferably is small enough that a pet's jaws may encompass at least its narrowest widths and, as a result, dispense dentifrice and actuate a scrubbing action to aid in cleaning teeth and the oral cavity of the pet generally. A flexibly, compressible and expandable outer containing layer 101 contains a dentifrice or other cleaning liquid, fluid or gel ("fluid") 103 in a cavity 104, which is variably dispensable to assist in cleaning the oral cavity of a pet, preferably, a mammalian pet. As will be explained in greater detail below, fluid 103 may be dispensed to the oral cavity of a mammalian pet by biting action, via bite-dispensing, cleaning-featured openings, such as those examples shown as 105, that are designed to accept variably-sized biting teeth. In addition, projections and/or textures, such as projections 107, provide natural abrasion, massage, polishing and/or scrubbing, also driven by biting action. A refilling port 109 permits the filling or refilling of cavity 104 from a complementarily-shaped intermediate fluid storage container 111, which may contain additional or differing fluid 103 and/or 106 such as, as its label is pictured to indicate, toothpaste. Preferably, port 109 is round, cylindrical or conical or otherwise has radial symmetry and comprises a one-way fluid valve, permitting the influx of fluid as shown by fluid motion arrow 113, but which prevents outward flow of fluid, out of cavity 104 through port 109, as shown by stricken fluid arrow 115.

FIG. 1 illustrates a variety of possible exemplary cleaning-featured openings. For example, opening 117 is an exemplary one-way valve opening, with elastomeric variably cavity enclosing features 119. In a resting state, features 119 converge with one another and prevent the outward flow of fluid from cavity 104. However, if a tooth, such as a mammalian tooth, enters opening 117 deeply enough, or with sufficient lateral pressure against them or surrounding, attached material, features 119 may be pulled or pushed away from one another, permitting the outward flow of fluid. Preferably, the overall design of cleaning featured openings, such as 117, alone or in combination with surrounding material shapes and properties, tends to channel teeth and other biting projections that are pressed against CLEANCHEW 100 substantially into the center of the openings. Another preferred form of cleaning-featured opening is shown as opening 121, and will be discussed in greater detail with reference to FIG. 2.

Another preferred form of cleaning-featured opening is shown as 123, which has a tricuspid one-way valve opening, with three semi-flexible flaps 124 to prevent escape of liquid, fluid or gel 103, unless and until a member, such as a tooth, pushes them away from one another (open) with the aid of optional tooth-action-facing, complementarily-shaped push members 125. 123 is shown in enhanced detail by a second rendering in a zoomed in window in FIG. 1.

Another preferred form of cleaning-featured opening is shown as 127, which comprises a sealing membrane 128 that may be pierced by animal biting and which may be scored to then create flaps that still resist the flow of liquid, fluid or gel 103 out of the CLEANCHEW to some degree, but that then permit 103 to flow onto the teeth and gums of the biting animal. An additional stop-cock or gravity ball valve (such as those used for animal water dispensers, and which close when pointed downward, at the gravitational bottom of the CLEANCHEW, may aid in preventing gravitational draining of the CLEANCHEW.

Another preferred form of cleaning-featured opening is shown as 129, with a zoom window to enhance detail, which comprises multiple hinged or flexible attached leaves 131, each of which, by itself, if driven by outward-flowing liquid, fluid or gel 103, substantially close opening 129, but any or all of which may again be forced open by a biting action or tooth.

Although a limited group of cleaning-featured openings and projections are shown at the top of the CLEANCHEW shown in FIG. 1, it should be understood that such cleaning-featured openings, projections and other cleaning textures and aspects disclosed in this application may cover substantially all bite or oral interfacing surfaces of a CLEANCHEW, or select regions better positioned to affect cleaning of an oral cavity or other cavity of an animal.

Figure 2:
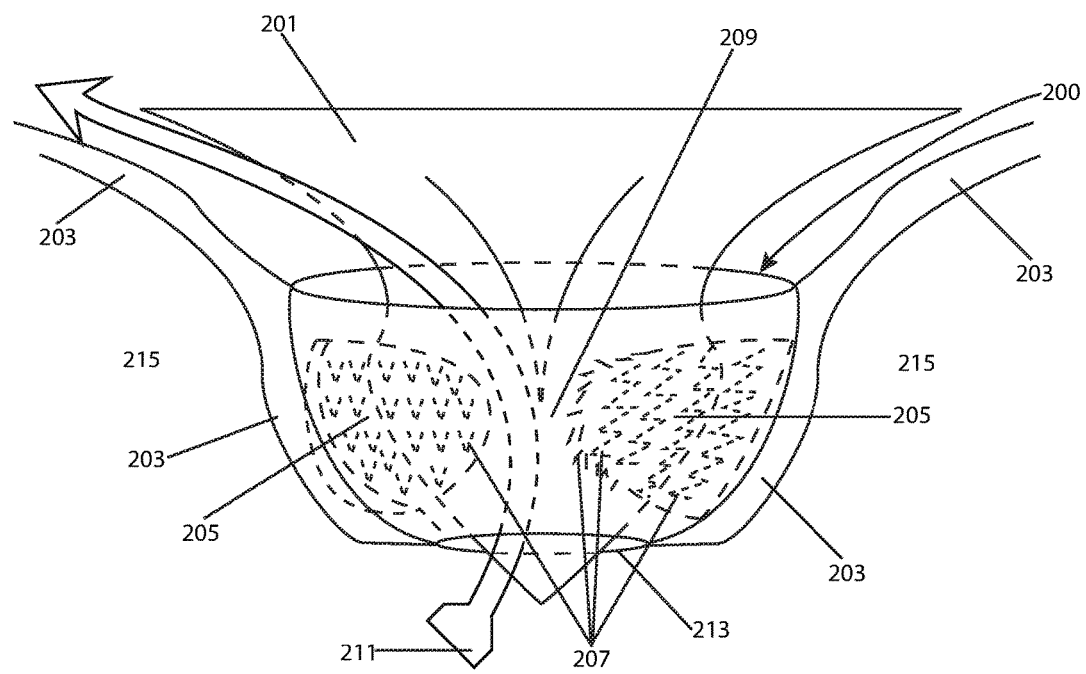
FIG. 2 is a side perspective view of an exemplary cleaning-featured opening 200, in an outer fluid containing layer of a CLEANCHEW, such as the CLEANCHEW shown in FIG. 1.

FIG. 2 is a side perspective view of an exemplary cleaning-featured opening 200, in an outer fluid containing layer of a CLEANCHEW, such as the CLEANCHEW shown in FIG. 1. A mammalian tooth 201 has substantially entered opening 200 due to a biting action of the mammal into and/or against the outer layer of the CLEANCHEW of which it is a part. The outer layer of the CLEANCHEW in which both the cleaning featured opening 200 and the tooth 201 are embedded, is partially shown as 203. Lining the outer surface of cleaning-featured opening 200 are scrubbing surface features 205, which preferably comprise and are at least partially surface-covered by scrubbing and fluid-absorbing projections, such as the projections shown as 207. As the mammal bites, and tooth 201 enters opening 200, projections 207 drag and/or rub against tooth 201, aided by surface tension of the outer surfaces of opening 200, and thereby scrub the surface of tooth 201. Features 205 and/or projections 207 preferably do not cover the entire outer surface of opening 200, and therefore abut surface gaps between them such as that shown as 209. As a result, when a tooth has penetrated opening 200, features 205 and projections 207 further serve as towers which vault the outer surface of opening 200 between them, and temporarily (as long as the tooth remains embedded in opening 200) permit the outward flow of fluid through the resulting volumetric gap, as shown, for example, by fluid motion arrow 211.

An inside port 213 of opening 200 is, when in the CLEANCHEW is in a resting state, substantially closed, and prevents the outward flow of material via elastomeric properties of the material comprised by the opening. However, when a tooth, such as tooth 201, enters opening 200, and therefore stretches its outer surface, port 213 may be pulled open due to the semi-flexible, semi-rigid nature of the material comprised in the outer layer and/or its surface, temporarily permitting the outward flow of fluid contained in cavity 215.

Figure 3:
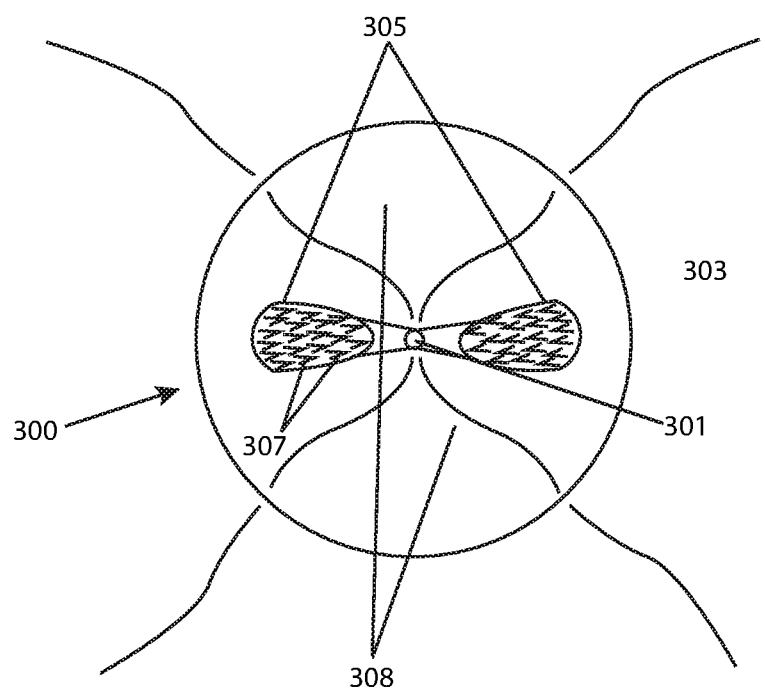
FIG. 3 is a top view of the same cleaning-featured variable opening as that depicted in FIG. 2, and serves to illustrate further exemplary aspects of the present invention.

FIG. 3 is a top view of the same cleaning-featured variable opening 300 pictured in FIG. 2, and serves to illustrate further exemplary aspects of the present invention. In the instance of FIG. 3, a tooth is not shown penetrating opening 300 and, as a result, the inside port, now shown as 301, is substantially closed in its undisturbed, resting conformation, preventing the outward flow (which would correspond with upward, out-of-the-page or positive z-axis flow in the figure) of fluid from the fluid containing side of layer 303, in which cleaning-featured opening 300 is embedded. In this resting conformational state, scrubbing features, such as 305, and projections, such as 307, may be seen in an unobstructed top view, and are contracted into a position substantially tighter (with less space between them) than the volume that would be occupied by a tooth if sufficiently embedded into the opening 300 and between them, which would therefore create tension that could be used for scrubbing against any such tooth. Tooth-guiding channels, exemplary edges of which are shown as 308, are also illustrated more clearly from the top-view, and extend beyond the depression in containing layer 303 comprised by opening 300, illustrating how, regardless of where a tooth happens to land on the surface of a CLEANCHEW, it may be guided into a cleaning-featured opening, such as that featured as 300. Of course, a wide variety of alternate channeling feature shapes may be used, aside from those partially illustrated as sloping downward (into the page of the figure) and towards the center of port 301 in a parabolic or otherwise curved shape, as shown in FIG. 3. Such alternate channeling feature shapes may also comprise abrading or scrubbing sub-features, which, as with other scrubbing features discussed with respect to other figures, may be angled such that their edges better catch the edges of debris and tartar from one, two, more or opposing directions of tooth movement. As such, configurations of such sub-features may be used that are effective regardless of whether a tooth is moving inward or outward (e.g., due to biting, or opening) and/or twisting and scrubbing or brushing can be more efficient.

Figure 4:
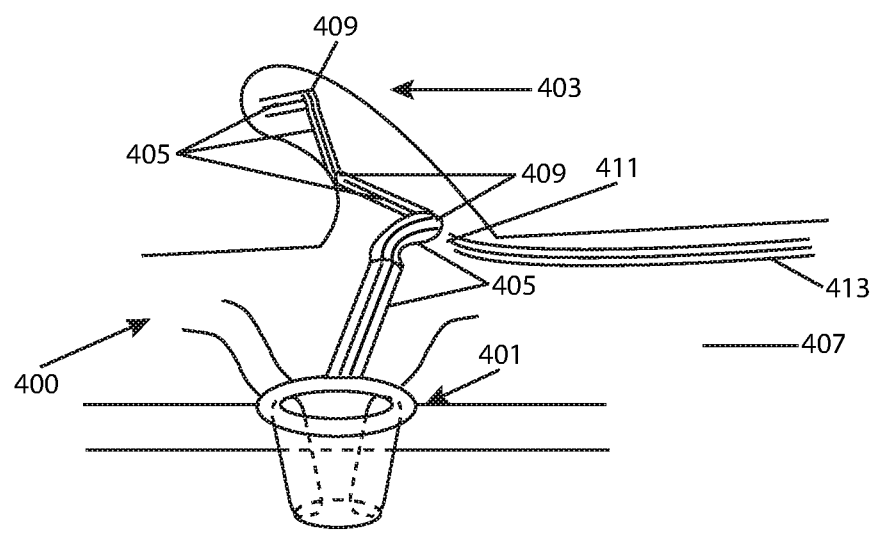
FIG. 4 is a side perspective view of an exemplary cleaning-featured variable opening and bite-induced shifting outward projection combination unit—specifically, a pairing— in its resting conformational structure, prior to biting or tooth penetration of a CLEANCHEW comprising the pairing.

FIG. 4 is a side perspective view of an exemplary cleaning-featured variable opening and bite-induced-shifting scrubbing outward projection combination unit —specifically, a pairing—in its resting conformational structure, prior to biting or tooth penetration of a CLEANCHEW comprising the pairing. In the pairing 400, a cleaning-featured variable opening 401 (for example, such openings of any style discussed elsewhere in this application or as illustrated in FIG. 4), is united with a scrubbing outward projection 403 (again, for example, such projections of any style discussed elsewhere in this application or as illustrated in FIG. 4) and is so united by connecting intermediate material, comprising a banded spring element(s) 405, which has/have both (1) resting and (2) biting-actuated conformational structures, which lead to different resting and biting-actuated conformational structures in surrounding attached flexible layer(s) or surface materials 407, which is, preferably, an elastomeric material or fabric and in which spring element(s) 405 are embedded and/or connected. Spring element(s) 405 are shown in its/their resting conformational state, meaning that the CLEANCHEW comprising it/them is not currently being bitten, or, at least not in or about the location of the pairing 400. In this state, the resting surface tension of surrounding material 407 may lead spring element (s) 405 to be compressed, as by non-deformational bends and/or compressions 409. In addition, tension-reducing or -breaking bend 411 may variably separate or reduce connections or spring aspects in neighboring material, such as neighboring spring element(s) 413 from spring element(s) 405. In this state, that resting surface tension and/or the resting conformational state of spring element(s) 405 and 413 and their variable connections, may lead projection 403 to be in a curved, leftward facing structural state. However, as will be discussed in greater detail with respect to FIG. 5, when bitten, chewed or otherwise physically insulted, alternate conformational states due to changes in surface tension may lead projection 403 to move into a different structural position, and resultantly brush teeth, gums and/or other oral cavity aspects that the projection may be in contact with. As suggested above, a pairing of one exemplary cleaning-featured variable opening and one bite-induced shifting scrubbing outward projection is exemplary only, and triplets, quartets and much more complex interacting physical relationships between variable openings and bite-induced shifting scrubbing outward projections and/or comprised or related spring elements may be, alternatively, used in accordance with aspects of the present invention, including, but not limited to, relationships where bite-driving of more distant openings, or other differently spaced openings, lead to different conformational results for projections that are more likely to effectively brush a surface area of a pet's mouth at that distance. For example, spring bands aligning (actuated conformation) with more distant openings only may lead to brushing in directions conforming with the roof of a mouth, rather than, for example, a curved massaging actuation motion which may be created closer to tooth gums.

Figure 5:
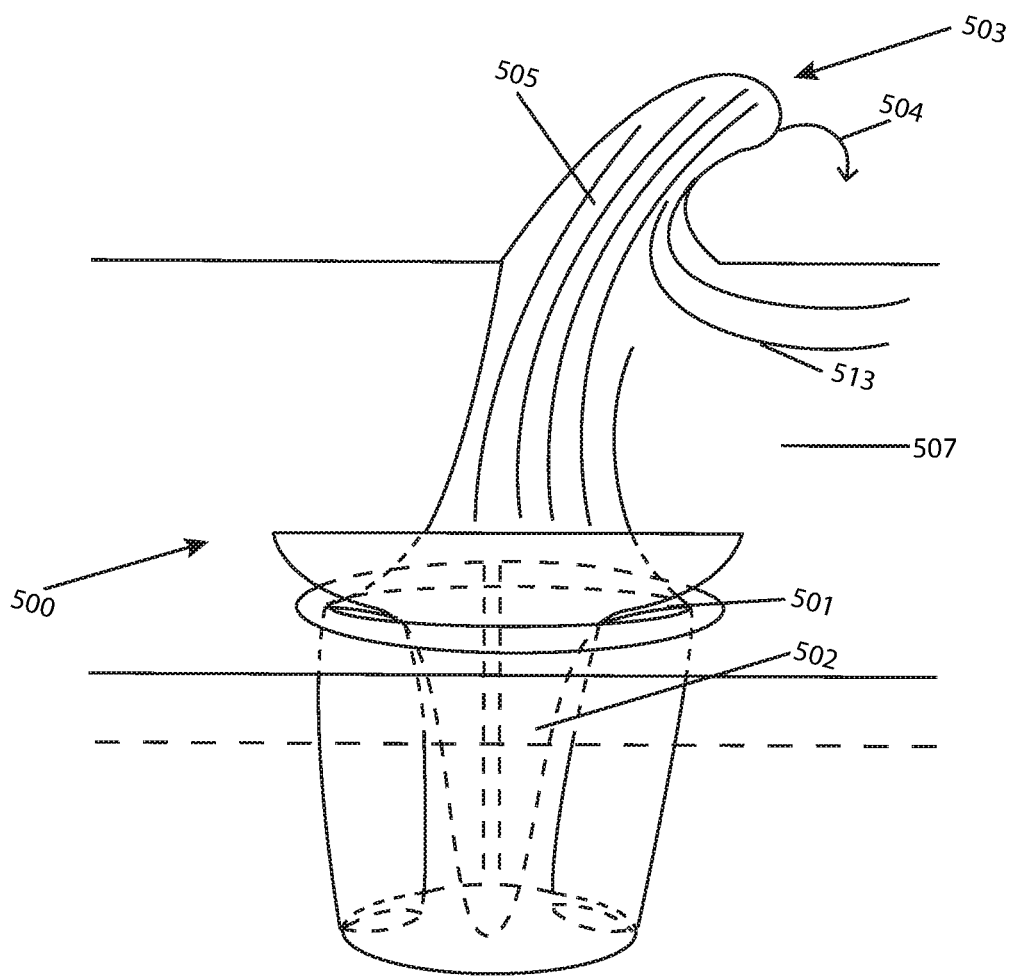
FIG. 5 is another view, from the same perspective, of the same exemplary pairing as that illustrated in FIG. 4, but in another conformation resulting from biting and tooth penetration of the pairing.

FIG. 5 is another view, from the same perspective except that some aspects have been enlarged, of the same exemplary pairing 400, as that illustrated in FIG. 4, but in another structural conformation resulting from biting and tooth penetration of the variable opening 401 of the pairing. Thus, in FIG. 5, a tooth 502 is illustrated as inserted into variable opening 501, creating both downward and outward pressure on opening 501 and creating surface tension in surface materials 507. More specifically, that pressure tends to align banded spring elements 505, to remove conformational folds. More straightened and aligned elements 505 and 513 then approach and achieve a conformational state in which folds disappear and the elements apply a rightward, curving motion in the scrubbing outward projection 503. That motion is illustrated by motion arrow 504, and may aid in scrubbing gums and neighboring teeth.

Spring element(s) 505 preferably have multiple stable resting conformations that may be switched by biting or other interaction with the surface of the CLEANCHEW. In addition, although this application has stressed biting-actuation for causing a shift from and to resting stable or other conformations of spring elements 405, and driving scrubbing projections and features, it should be noted that such spring elements may instead, or in addition, drive dilation and contraction of CLEANCHEW surface variable openings such that, when a projection or other surface feature is sufficiently bent over or pulled sideways or compressed by rubbing against a surface to be cleaned, then and only then are spring elements aligned that cause outward, opening tension on the rims and surfaces of fluid, gel and/or liquid-containing orifices. Also preferably, intermediate fluid, gel and/or liquid-containing antechamber(s), preferably abutting, variably opening into and smaller than a main fluid, gel and/or liquid-containing cavity, and also abutting and sharing the variable opening(s) to the surface of the CLEANCHEW, receive such fluid, gel and/or liquid from the main cavity only by a variable valve which substantially closes during a sufficient scrubbing action that drives surface features sufficiently to cause the spring elements to drive dilation of CLEANCHEW surface variable openings. It should also be noted that, although separate spring elements and outer CLEANCHEW layer materials are discussed, a single material, with spring properties and resting conformational state(s) may instead be used as both the material layer and spring element(s), such that surface deformation or teeth acceptance may drive variable opening of both a main fluid, gel and/or liquid-containing chamber, and/or intermediate antechambers, into CLEANCHEW surface variable openings.

Figure 6:
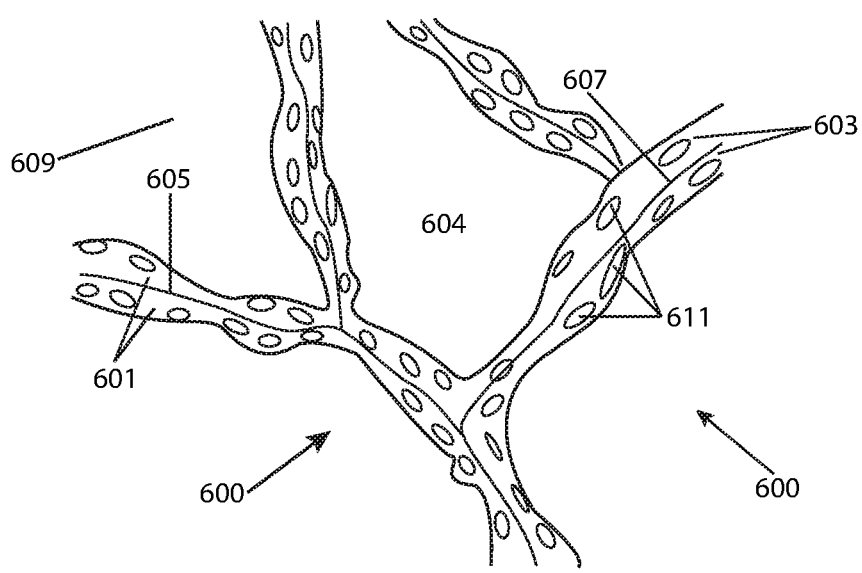
FIG. 6 is a partial top-view of exemplary bitable surface features of a CLEANCHEW, in accordance with additional aspects of the present invention.

FIG. 6 is a partial top-view of exemplary bitable surface features of a CLEANCHEW, in accordance with additional aspects of the present invention. Reticulated or interspersed grooves, such as those depicted as 600, comprise converging channel sides, such as those shown as converging channel side pairings 601 and 603. Such converging channel sides are within an outer CLEANCHEW material layer the outer surface of which is labeled 604, and may, when a tooth penetrates between where converging channel sides meet (such as that shown as convergences 605 and 607) separate sufficiently to permit a fluid from a contained cavity to flow outward (toward the viewer of the figure), and toward the penetrating tooth and gums in which the tooth may be embedded. The meeting points of the converging channel sides are more distant from the viewer of the picture than the main surface 609 of the outer layer of the CLEANCHEW—meaning that as converging side pairs such as 601 and 603 converge, to extend the example, at convergences 605 and 607, respectively, their surfaces slope inward, into the page, away from the viewer of the figure as they slope toward their convergences. Lining the outer surface of converging side pairings, such as 601 and 603, are scrubbing surface features, such as those shown as 611, which preferably comprise and are at least partially surface-covered by scrubbing and fluid absorbing projections, such as those discussed elsewhere in this application, and all of such features facilitate both scrubbing and the creation of temporary fluid-escape gaps during animal biting of the CLEANCHEW.

Figure 7:
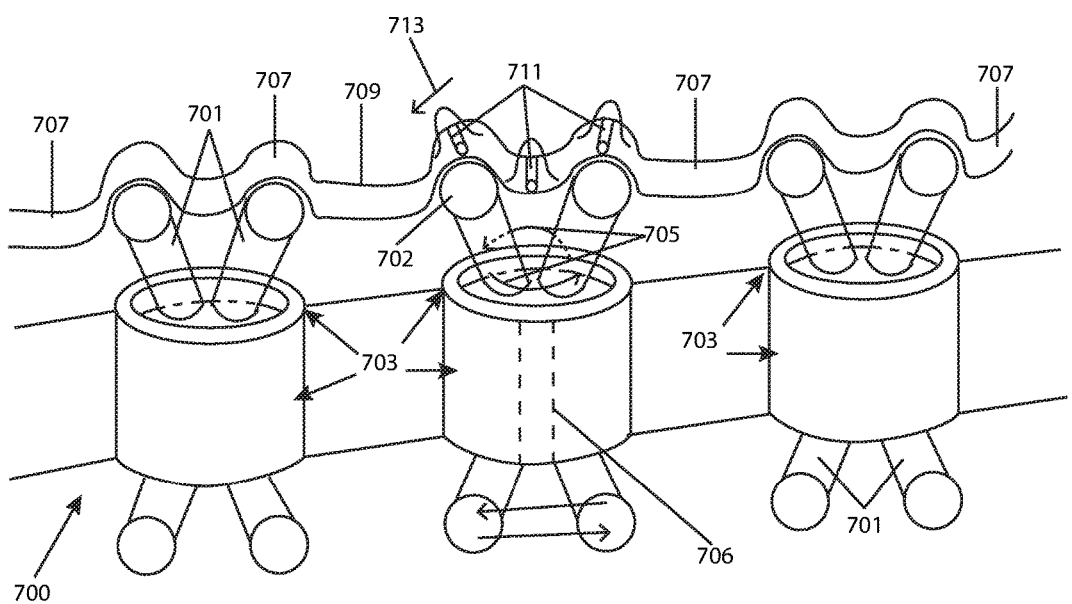
FIG. 7 is a side-view of part of a CLEANCHEW that includes biting- and/or motor-actuable movable structural members.

FIG. 7 is a side-view of aspects of a CLEANCHEW 700 that comprises biting- and/or motor-actuable movable structural members. Major biting- and/or motor-actuable movable structural members, such as those shown as examples 701, and which are generally cylindrical but with semi-spherical tops such as that shown as 702, extend from and are mounted to movable ball-and-socket, turret or swivel joints 703, about which they may rotate, as shown by exemplary rotational motion arrows 705 in the instance of a swivel joint (swiveling around a circular rotation axel, such as axel 706), or those major members may rotate in any spherical direction, in the instance of a ball-and-socket or turret joint. Major members 701 are buried beneath outer CLEANCHEW containing layer 707 (layer 707 being shown in vertical cross-section to avoid blocking the view of other aspects of the invention), which is preferably made of an elastomeric or flexible yet deformation-resistant material. Preferably, layer 707 is stretched over major members such as 701 with sufficient tension that the members are in contact with and variably shape (with their motion within joints 703) the surface layer 707. Such contact also aids in permitting biting on the outer surface of the layer 709 to drive motion of the major members such as 701. But, optionally or in addition, joints 703 may also be driven by servo/motors. Either way, the resulting moving surface shapes of layer 707 result in scrubbing and massaging of gums and teeth of an animal biting into layer 707 with its teeth. Minor biting- and/or motor-actuable movable structural members, such as the examples shown as 711, are preferably smaller than major members 701, and may be embedded in layer 707, and may move both in reaction to the same animal biting (which, as discussed above, may drive the motion of major members 701), and in reaction to motion of the major members, which may push minor members 711 upward and/or downward and/or rotate them about lever rotational axes. Minor member 711, therefore, are or create motion-variable scrubbing/massaging sub-features in layer 707, in which they are embedded. For example, if major members 701 move as shown in the second joint from the left of the illustration by motion arrows 705, the top of the left-most minor member may move into the page and to the left, in reaction, as shown by motion arrow 713.

Figure 8:
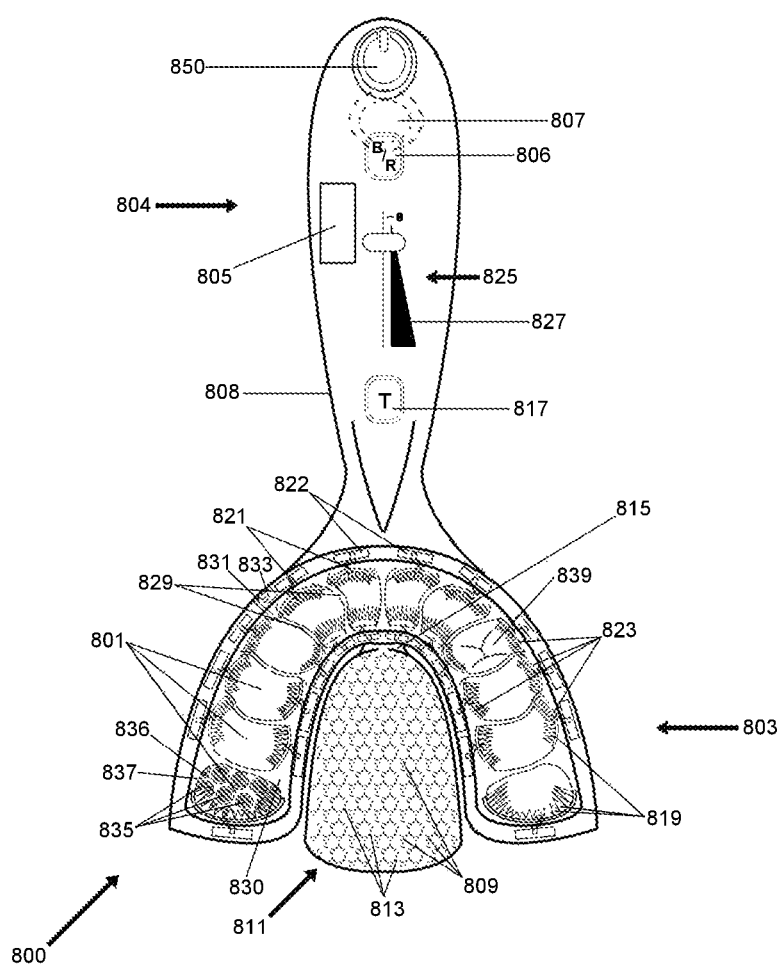
FIG. 8 is a top view of a high-speed, bite-actuable device for cleaning the teeth and oral cavity of a mammalian animal.

FIG. 8 is a top view of a high-speed, bite-actuable device 800, for cleaning the teeth and oral cavity of a mammalian animal. More specifically, device 800 is custom-fitted to accommodate the teeth and oral cavity of a human user (not pictured), and may be actuated by placement or a single bite by the user causing the users teeth to enter scrubbing channels, such as the exemplary scrubbing channels 801, of device 800.

Generally speaking, device 800 comprises a cleaning head end 803 and a handle grip end 804. By holding grip end 804, a user of device 800 may insert cleaning head end 803 into his or her mouth, with the upper side (pictured) positioned with each channel 801 below a tooth of his or her upper jaw. In some embodiments, which will be discussed further below, and in reference to FIGS. 9 and 10, a user may power on and cause moving cleaning parts of head end 803 to begin moving and working simply by biting down, and inserting his or her teeth into channels 801. More specifically, sensors—such as but not limited to pressure sensors—may sense that insertion of teeth and/or other mouth contact and, when device 800 is sensed to be correctly placed and the user's teeth are completely inserted (with sufficient amount and/or points of pressure detected in head end 803), a control system 805 within device 800 electrically connected or otherwise in communication with those sensors may power on and/or begin actuating cleaning features within head end 803, scrubbing the user's teeth. In some embodiments, such sensor-driven actuation may take place when a mode has been activated or has not been deactivated, for example, by a bite-response mode activation button 806, electrically connected with or otherwise able to communicate with control system 805. In such embodiments, a user and/or the control system may disable bite-response mode and, in such cases, the actuation of scrubbing features in head end 803 may be initiated simply by powering on device 800—for example, by depressing power button 850. Control system 805 may be a control system such as that discussed in reference to FIG. 10, below.

Prior to the placement and actuation of device 800 discussed herein, a user preferably wets and fills device 800 with water and a dentifrice—such as toothpaste. To do so, a user may directly wet and fill channels 801. However, in some embodiments, internal channels and/or pumps, within device 800 allow the filling of toothpaste and/or water cavity(ies), also within device 800. In one preferred embodiment, a filling port 807 in the housing 808 of device 800 may permit the filling of a storage cavity and fluid-directing channels within device 800. For simplicity of presentation, that cavity and channels are not pictured, but it should be understood that they may allow the storage and flow of fluid (such as water and dentifrice) from port 807 to the teeth-accepting scrubbing channels 801, as well as to exit ports, such as exemplary ports 809, of a mouth epithelium-scrubbing brush unit 811. Brush unit 811 may also comprise scrubbing features such as exemplary projections or bristles 813. Brush unit 811 may be driven to rapidly move, preferably in a laterally shifting and/or circular motion, while generally maintaining its attitude, as pictured, and, thereby, device 800 scrubs and cleans the user's roof of the mouth and/or tongue (with a similar surface facing into the page, in the perspective of the drawing). Preferably, brush unit 811 is comprised of a compliant material, contoured to fit the roof of a user's mouth, tongue and other aspects of the epithelium of the user's mouth. Brush unit 811 may be driven by drive shaft 815, connected to a linear actuator or other motor (not pictured) within device 800 which is powered and driven by control system 805. In one embodiment, a user may cause brush unit 811 to be so actuated by control system 805, and/or may cause fluid to flow from and douse the outer surface of brush unit 811, by a user command—such as by a user depressing tongue brush activation button 817, which is electrically connected with or otherwise able to communicate signals with control unit 805.

Motor-driven projections or bristles, such as examples 819, are also preferably present within channels 801, and are attached to cam shafts, such as exemplary cam shafts 821, each of which may be driven by a local motor, such as exemplary rotary motors 822, or another, more universal cam. In one embodiment, such a universal cam strip, connected to several bristle heads, such as the examples shown as 823, (or directly to the bristles), may be driven by a single, larger motor within the handle grip end 804 (not pictured).

The speed, (and, in some embodiments, the direction(s), intensity, or other aspects) of the scrubbing bristle motions discussed above may be controlled by a user-actuable speed control—such as exemplary slider 825. Slider 825 is also preferably electrically connected or otherwise in communication with control system 805, which is so connected with and able to power the motor(s) driving bristles 813 and 819, as discussed above. In one embodiment, slider 825 increases the speed (and, in some embodiments, the direction(s), intensity, or other aspects) of the scrubbing bristles and other actuated cleaning features when actuated in the direction toward cleaning head 803, as indicated by a speed, intensity or other aspect linear degree indicator 827.

In addition to the scrubbing motions of bristles 813 and 819, the heads, cams and other moving parts discussed above, device 800 may power, drive and cause the actuation of other scrubbing moving parts, cleaning various aspects of a user's teeth and oral cavity when used as set forth in this application. Accordingly, in some embodiments, elastomeric flossing lines, such as examples 829, are included, the motion of which may be driven in part by the same cam shafts set forth above (such as examples 821). More specifically, flossing lines 829 may be part of or otherwise integral with a channel-lining elastomeric layer 830, which layer hugs, conforms with and flosses the sides of teeth as it moves with the rotation (or other, e.g., shifting, movement) of motors and cams driven by control system 805. As one example, pictured, when the cams 821 shift layer 830 downward and to the left, driving bristles in the same direction, layer 830 is also pulled in that same direction. Because flowing lines 829 encounter the upper-right edges between two of a user teeth, however, line examples 829 are pulled and moved against those tooth surfaces, cleaning them—which resulting conformation and position of lines 829 are shown (without the teeth causing those positions, for visibility). As cams 821 rotate 180 degrees away from the position pictured, however, the other side between a user's teeth will instead be cleaned by a corresponding, opposing motion of layer 830 and lines 829. In some embodiments, a dedicated cam shaft 831, drive shaft or drive line and/or motor 833 controlled by system 805 may be used to drive each of lines 829—in addition to the motor(s) or cam(s) driving bristles 819.

Some embodiments may comprise rotary brushes, driven by rotary motors, such as exemplary rotary brushes 835, shown lining the bottom 836 of channel 837, which faces the biting-surface of a tooth as it enters channel 837, cleaning at is pressed against them with a biting motion. In some embodiments of device 800, however, channels 837 are also valves, lining a channel or other cavity comprising dentifrice (as discussed elsewhere in this application). In such embodiments, as a tooth enters a valve/channel (such as exemplary quad-cuspid valve/channel 839) it unseals the valve, and allows the penetrating tooth to be cleaned as the tooth is bathed in the fluid held in the valve. As with other valves set forth in this application, and as pictured in exemplary valve channel 839, such valves may be one-way (check valves), preventing the escape of fluid from device 800 even when opened and filled with a penetrating tooth. Also as set forth in other parts of this application, spacers for allowing some amount of fluid escape, bristles or other cleaning features may be included lining parts of tooth-interfacing surfaces of the valve, such as valve example 839.

As explained further below, control system 805 may be connected to a power source, such as a rechargeable battery and/or capacitor (not pictured) which preferably is present within device 800 and grip end 804. However, in some embodiments, device 800 may be externally powered (e.g., by ambient electromagnetic power).

Although not visible from the perspective of the figure, it should be understood that another side of cleaning head end 803, with tooth-scrubbing channels similar to those pictured as 801, but designed to conform to the shape of a user's teeth inset in his or her lower jaw—rather than her upper jaw, as pictured—may, and preferably is, also included in device 800. Thus, by biting into cleaning end 803, with a tooth entering each channel and/or valve of cleaning end 803, a user's full set of teeth and be completely, quickly cleaned.

In some embodiments, port 807, and the cavities and channels connected with it, and channels 801 and brush unit 811 may be flushed at once by inserting a water faucet end into port 807, forming a seal between them. In such embodiments, port 807 preferably has a ramped, elastomeric profile, enabling a seal between it and a wide variety of faucet sizes and types.

Figure 9:
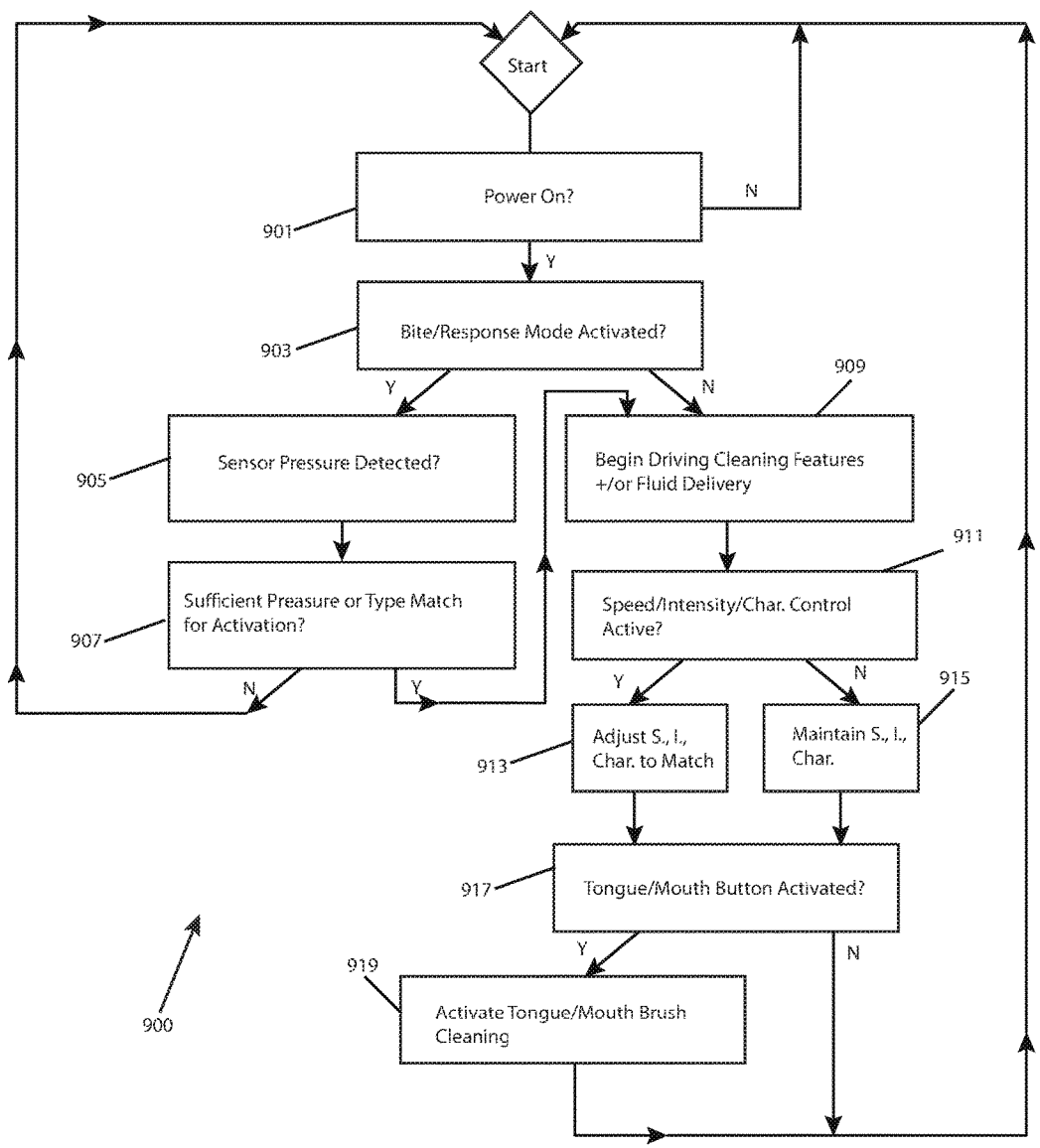
FIG. 9 is a process flow diagram depicting exemplary steps that may taken by a control system carrying out aspects of the present invention.

FIG. 9 is a process flow diagram depicting exemplary steps that may taken by a control system carrying out aspects of the present invention, such as the control systems discussed above, and in reference to FIG. 10, below, controlling bite-actuable cleaning device 800. Beginning with step 901, the control system first determines whether the device has been powered on, for example, by a user depressing power button 850. (It should be noted that, in some embodiments, device 800 may power itself on by passive or separately-powered sensors detecting a sufficient amount or pattern of pressure associated with use of the device. Such amounts and patterns of pressure or other stimulus will be discussed in greater detail below. If device 800 has been powered on, in some embodiments, the control system proceeds to step 903, where it determines whether a "Bite/Response Mode" has been activated—for example, by detecting whether button 806 has been depressed. If so, in step 905, the control system may next determine whether sensors detect pressure or other activity—for example, from sensors detecting user biting pressure within end 803 of device 800. If that pressure or activity is detected, the control system then proceeds to step 907, wherein it determines whether the pressure matches a recording or setting matching proper use of device 800, for example by teeth properly seating in channel/valves 801. For example, the control system may determine if a sufficient number of channels/valves have been penetrated, and whether they are fully penetrated (e.g., by detectors of whether the valves have been forced open by penetrating teeth.) In some embodiments, the control system compares data from the pressure sensors to pre-stored data or descriptive parameters for sensor data associated with such proper seating and, if sufficiently matching, powers and drives the cleaning features and fluid transmission aspects of end 803 discussed above, in step 909. If the Bite/Response Mode has not been activated, the control system may also begin powering and driving those features and aspects directly.

Proceeding to step 911, the control system next may take readings from a cleaning speed, intensity or other device characteristic control—such as, but not limited to the exemplary slider 825, discussed above—if such a control has been activated. If so, the control system may proceed to step 913, in which it alters the driving power or other characteristics to match the selected settings. If such a control has not been activated, the control system may proceed to step 915, in which it maintains its existing power or other characteristics necessary to drive the cleaning features of device 800 in accordance with default or previously-existing settings.

Next, the control system may proceed to step 917, in which it determines whether a tongue and mouth brush, and/or other mouth epithelium device (such as device 811), have been activated—for example, by detecting whether button 817 has been depressed. If so, the control system may begin to power and drive such a device in step 919. The control system then returns to the starting position.

Figure 10:
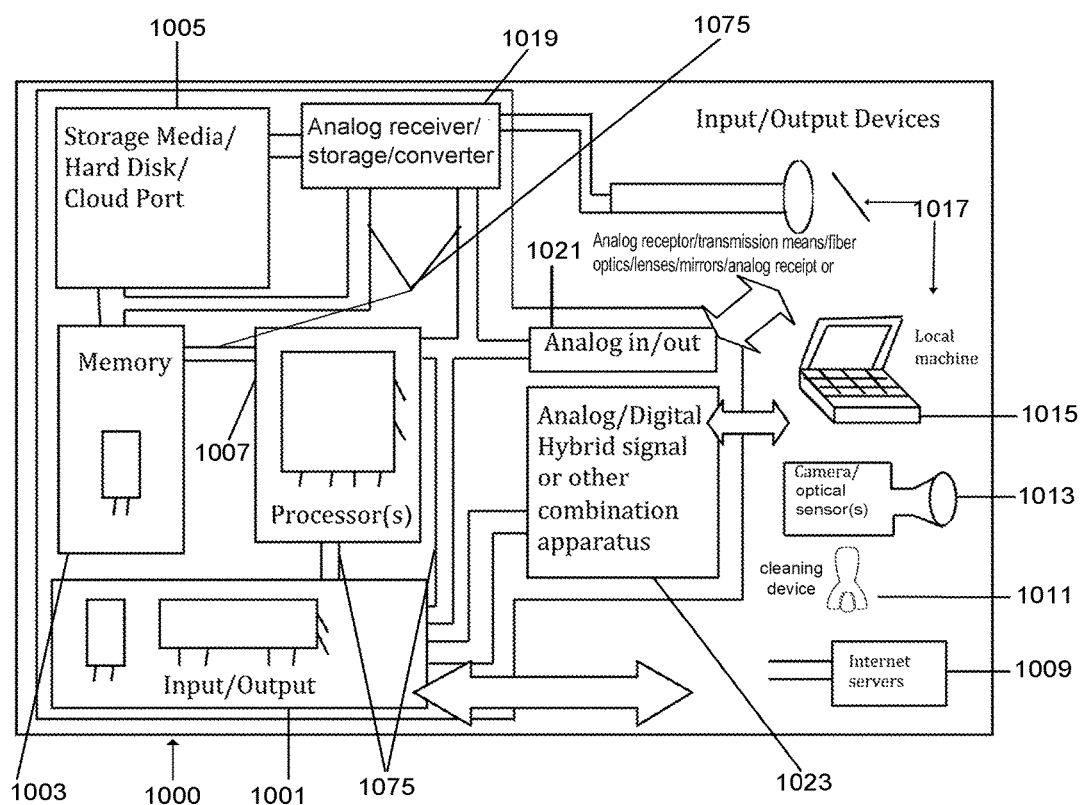
FIG. 10 is a schematic block diagram of some elements of an exemplary control system that may be used in accordance with aspects of the present invention

FIG. 10 is a schematic block diagram of some elements of an exemplary control system 1000 that may be used in accordance with aspects of the present invention, such as, but not limited to, sensing gas and physical member compression and gas concentrations and actuating servo/motors and control valves, and receiving control commands and managing input interfaces from a Control and Command, as defined and discussed elsewhere in this application. The generic and other components and aspects described herein are not exhaustive of the many different systems and variations, including a number of possible hardware aspects and machine-readable media that might be used, in accordance with the present invention. Rather, the system 1000 is described to make clear how aspects may be implemented. Among other components, the system 1000 includes an input/output device 1001, a memory device 1003, storage media and/or hard disk recorder and/or cloud storage port or connection device 1005, and a processor or processors 1007. The processor(s) 1007 is (are) capable of receiving, interpreting, processing and manipulating signals and executing instructions for further processing and for output, pre-output or storage in and outside of the system. The processor(s) 1007 may be general or multipurpose, single- or multi-threaded, and may have a single core or several processor cores, including microprocessors. Among other things, the processor(s) 1007 is/are capable of processing signals and instructions for the input/output device 1001, analog receiver/storage/converter device 1019, and/or analog in/out device 1021, to cause a display, light-affecting apparatus and/or other user interface with active physical controls to be provided for use by a user on hardware, such as a personal computer monitor (including, but not limited to, monitors or touch-actuable displays) or terminal monitor with a mouse and keyboard or other input hardware and presentation and input software (as in a GUI), and/or other physical controls.

For example, and with particular emphasis on the aspects discussed above, in connection with FIGS. 8 and 9, the system may carry out any aspects of the present invention as necessary with associated hardware and using specialized software, including, but not limited to, GUI and other user interface aspects that may present a user with options for cleaning modes, bristle and other scrubbing actuation, and speed and intensity controls. As another example, the system may detect pressures and characteristics from bite sensors, controlling valves to release fluids and scrubbing features to clean teeth when sensor measurements and timing match a properly positioned and biting set of mammalian teeth engaged with the cleaning end of a device comprising said system (such as device 800).

The processor 1007 is capable of processing instructions stored in memory devices 1005 and/or 1003 (or ROM or RAM), and may communicate via system buses 1075. Input/output device 1001 is capable of input/output operations for the system, and may include any number of input and/or output hardware, such as a computer mouse, keyboard, networked or connected second computer, camera(s) or scanner(s), sensor(s), sensor/motor(s), range-finders, GPS systems, other Command and Control centers, electromagnetic actuator(s), mixing board, reel-to-reel tape recorder, external hard disk recorder, additional hardware controls and actuators, directional shading matrices, directionally-actuable light sources with variable collimation and shiftable bases, additional movie and/or sound editing system or gear, speakers, external filter, amp, preamp, equalizer, computer display screen or touch screen. It is to be understood that the input and output of the system may be in any useable form, including, but not limited to, signals, data, and commands/ instructions. Such a display device or unit and other input/output devices could implement a user interface created by machine-readable means, such as software, permitting the user to carry out the user settings, commands and input discussed in this application.

1001, 1003, 1005, 1007, 1019, 1021 and 1023 are connected and able to communicate communications, transmissions and instructions via system busses 1075. Storage media and/or hard disk recorder and/or cloud storage port or connection device 1005 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive.

Generally speaking, the system may be implemented as a client/server arrangement, where features of the invention are performed on a remote server, networked to the client and made a client and server by software on both the client computer and server computer. Input and output devices may deliver their input and receive output by any known means of communicating and/or transmitting communications, signals, commands and/or data input/output, including, but not limited to, the examples shown as 1017, such as 1009, 1011, 1013 and 1015 and any other devices, hardware or other input/output generating and receiving aspects. Any phenomenon that may be sensed may be managed, manipulated and distributed and may be taken or converted as input or output through any sensor or carrier known in the art. In addition, directly carried elements (for example a light stream taken by fiber optics from a view of a scene) may be directly managed, manipulated and distributed in whole or in part to enhance output, and whole ambient light information for an environmental region may be taken by a series of sensors dedicated to angles of detection, or an omnidirectional sensor or series of sensors which record direction as well as the presence of photons recorded, and may exclude the need for lenses or point sensors (or ignore or re-purpose sensors "out of focal plane" for detecting bokeh information or enhancing resolution as focal lengths and apertures are selected), only later to be analyzed and rendered into focal planes or fields of a user's choice through the system. While this example is illustrative, it is understood that any form of electromagnetism, compression wave or other sensory phenomenon may include such sensory directional and 3D locational information, which may also be made possible by multiple locations of sensing, preferably, in a similar, if not identical, time frame. The system may condition, select all or part of, alter and/or generate composites from all or part of such direct or analog image transmissions, and may combine them with other forms of image data, such as digital image files, if such direct or data encoded sources are used.

While the illustrated system example 1000 may be helpful to understand the implementation of aspects of the invention, it is understood that any form of computer system may be used to implement many aspects of the invention—for example, a simpler computer system containing just a processor (datapath and control) for executing instructions from a memory or transmission source. The aspects or features set forth may be implemented with, and in any combination of, digital electronic circuitry, hardware, software, firmware, or in analog or direct (such as light-based or analog electronic or magnetic or direct transmission, without translation and the attendant degradation, of the image medium) circuitry or associational storage and transmission, any of which may be aided with external detail or aspect enhancing media from external hardware and software, optionally, by networked connection, such as by LAN, WAN or the many connections forming the internet. The system can be embodied in a tangibly-stored computer program, as by a machine-readable medium and propagated signal, for execution by a programmable processor. The method steps of the embodiments of the present invention may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

Figure 11:
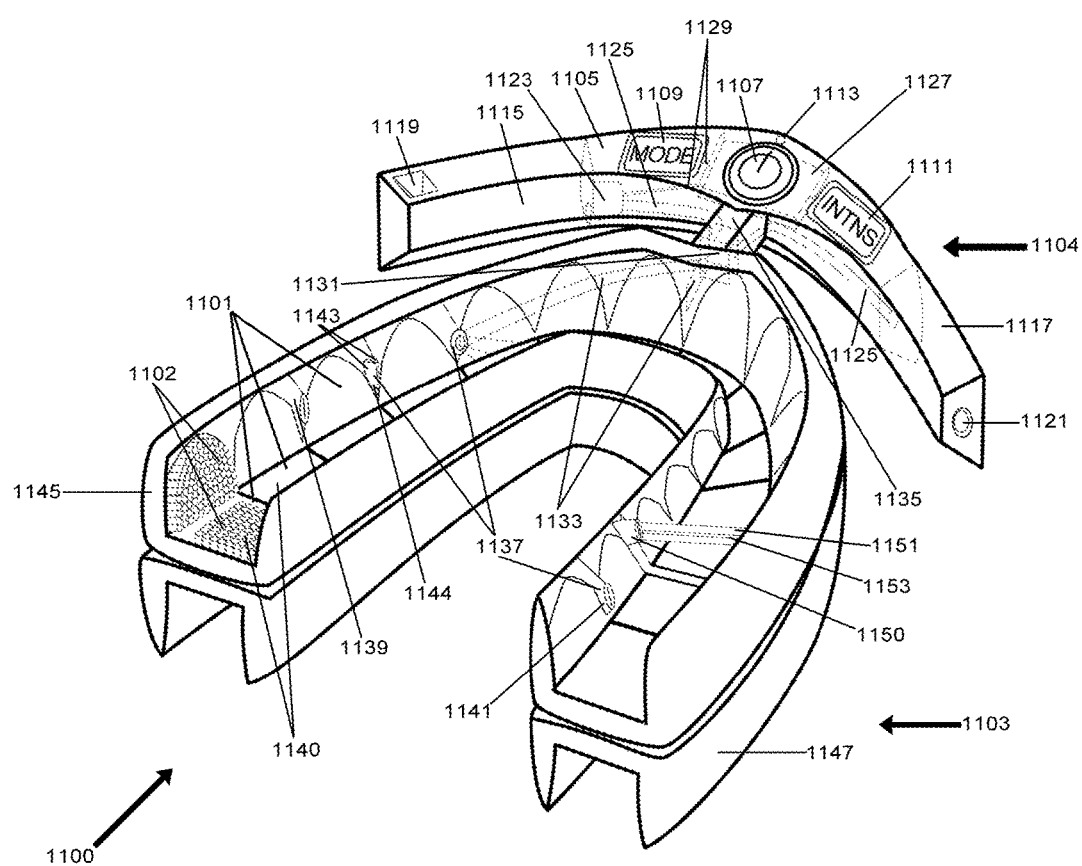
FIG. 11 is a perspective view of a new form of automatic oral hygiene device, which can be used to quickly and simultaneously brush and floss each of a user's teeth and, in some embodiments, other parts of a user's mouth.

FIG. 11 is a perspective view of a new form of automatic oral hygiene device 1100, which can be used to quickly and simultaneously brush and floss each of a user's teeth and, in some embodiments, other parts of a user's mouth. In some embodiments, which will be discussed in greater detail below, device 1100 can rapidly clean a user's entire oral cavity in under 30 seconds, with results exceeding the hygiene normally obtained with a conventional toothbrush. Some aspects of device 1100, such as the exemplary teeth-accepting channels 1101 and exemplary control system-actuable teeth-cleaning brushes 1102 on their surfaces (one example shown, only, for clarity of illustration—but it should be understood that such brushes preferably line each surface of the channels 1101), are similar in nature to that shown for toothbrushes discussed above. In the interests of brevity and clarity, not each of such repetitive aspects will be set forth again in full detail. However, several additional aspects are set forth in this figure in this section of the application.

Figure 12:
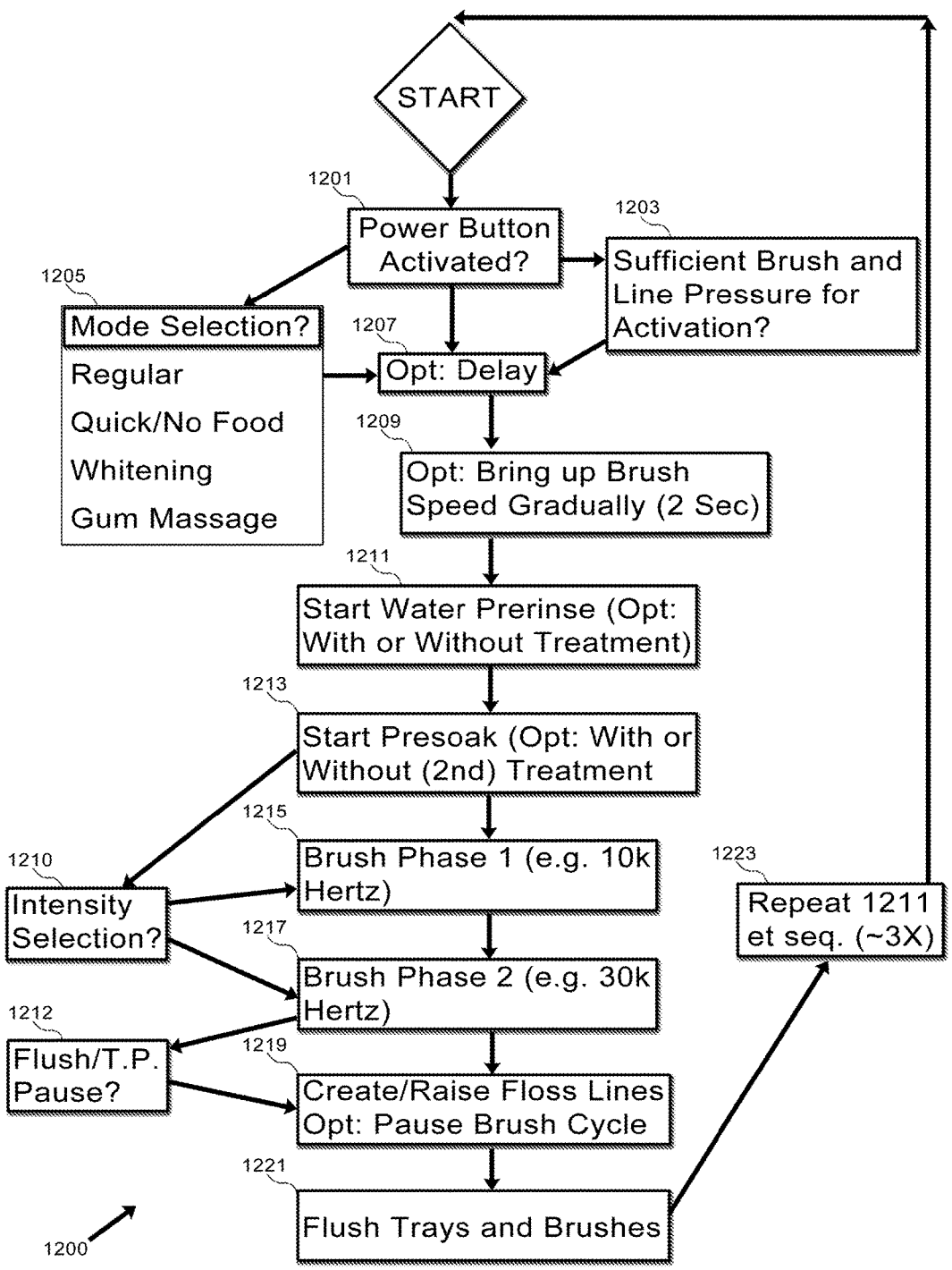
FIG. 12 is a process flow diagram depicting exemplary steps that may taken by a control system carrying out aspects of the present invention, such as the control systems discussed above, and in reference to FIG. 10, controlling bite-actuable cleaning device 1100.

For example, a generally crescent-shaped handle section 1104 is pictured. As with handle end 804 of device 800, discussed above, a user can grip handle section 1104 and insert a cleaning section (in this case, 1103) into his or her mouth, because these two major sections are physically and rigidly attached to one another. Although unconventional, and perhaps reducing some of the leverage and ease for maneuvering device 1100 than more conventional handles, the crescent-shaped configuration of handle 1104 has many other advantages, too numerous to set forth in detail here—several of which are unique to the oral hygiene techniques set forth in the present application. Generally speaking, handle 1104 has a wide range of horizontal handgrip positions, facilitating grip by a user's preferences and right or left hand equally. Also enhancing that grip, and the presentation and access of various user interface aspects, is an upward and user-facing surface panel 1105. The user interface aspects may include a main power button 1107, a mode selection button 1109, an intensity-adjusting button 1111, and a display, such as exemplary indicator light 1113. The function of each of such user interface aspects will be discussed herein in detail, below, as well as in reference to the techniques set forth in reference to the next figure (FIG. 12). Also within handle section 1104 are two holding tanks: Water/solvent tank 1115 and a dentifrice/treatment tank 1117, which may hold a toothpaste, tooth-treating chemicals and/or other dentifrice. Each of tanks 1115 and 1117 may be filled and refilled by a user, by pouring water or solvent into a valved opening 1119 to tank 1115, or by squeezing a toothpaste or other dentifrice into valved opening 1121 to tank 1117. Both of tanks 1115 and 1117 are preferably downward-sloped at their bases, and/or comprise pumps (such as exemplary pump 1123) to pump the fluid within them, toward and through distribution conduits—such as the examples set forth as 1125. Those pumps, the user interface aspects on panel 1105, sensors, and any other active aspects of device 1100 set forth herein may be controlled and powered by a control system 1127, such as the control system set forth above in reference to FIG. 10, which may be electrically connected and adapted for communications with those aspects via wiring (such as exemplary wiring 1129) and/or any other means of power and communications know in the art. In some embodiments, the fluid contents moved through distribution conduits 1125 may be first mixed, whipped or otherwise agitated in a mixing antechamber 1131, before being further pumped (not pictured) for distribution through secondary distribution conduits, such as the examples shown as 1133 (although shown just leading to a few exemplary line-creating ports, discussed below, it should be understood that a complex of many more such conduits, leading to and separately pressurized and controlled for each and every port by the control system, or, in some embodiments, to outer- or inner-facing ports, may be included). In some embodiments, the control system 1127 may alter the mixture and amounts of each fluid component from each of tanks 1115 and 1117, according to a mode or intensity selected by a user (using mode selection button 1109 or intensity selection button 1111 or, in some embodiments, data from sensors—for example, by metering out different amounts of fluid from each of tanks 1115 and 1117 through controlled valves or pumps conducting fluid from the tanks to mixing antechamber 1131. In any event, the mixed fluids (which may be, alternatively, isolated in separate distribution conduits, and released in controlled amounts at the point of use, a user's teeth) are next conducted to cleaning section 1103, across a bridge 1135 adjoining that section with handle section 1104, via secondary distribution conduits 1133.

Upon entering cleaning section 1103, the mixed fluids are sent to numerous ejection ports, such as exemplary ports 1137 which are and create flossing projections via the resulting ejection of fluids. Although the example of flossing line establishing ports 1137 are given, it should be understood that a wide variety of other extrusion ports, slides, diffusion matrices or transmission materials, siphons or other transmission techniques may, alternatively or in addition, be used to transmit the fluids into contact with the user's teeth, gums, and the remainder of his or her oral cavity. In the embodiment shown, the ejection of fluids through each of ports 1137 is preferably forcibly pulsed according to a timing and pattern of force set forth in the particular use mode selected by a user (and carried out by control system 1127). Also preferably, there are at least two ports, situated at a point of division between two tooth-cradling pockets (such as exemplary channels/pockets 1140), and dedicated to establishing flossing lines between each gap in a pair of user's teeth. One of those ports, such as exemplary port 1139, is located at the outward-facing surface of the user's teeth, while the other, such as exemplary port 1141, is located at the inward-facing surface of the user's teeth, when a user has placed section 1103 within his or her mouth, and inserted each of her teeth into pockets 1140. Preferably, in most usage modes, only one of each of those two opposing pairs of ports at each gap is active, ejecting the fluid, at a given time, and the force with which it is expelled is sufficient to fully penetrate and clean the gap between the user's teeth to which the pair of ports is dedicated, as well as the gap between the teeth and gums. To prevent fluid from the active port entering the opposing, inactive port, port-tightening water-foils 1143 may be included about the outer surface of each port—as shown in exemplary port 1144. In some embodiments, such as that pictured with exemplary port, the material comprising the flossing lines that they create may be more rigid than with the use of an ejected fluid. In the example pictured with port 1150, for instance, a flattened flossing tape 1151 is gripped by a pair of opposing ports (of which port 1150 is one). In some embodiments, such flossing tape 1151 may have central ridges 1153 with edges to aid in brushing between the user's teeth. This is especially effective in embodiments, such as that pictured for port 1150, where the control system can raise, lower and vibrate the flossing line (with motors attached to each of the ports, and an open channel for port 1150 to travel within) between the user's teeth, and even under the gums by actuating the angle of the tape (e.g., with a rotary motor or gimble changing the angle of the leading edge of the floss line). Similarly, with fluid floss lines, the flossing fluid ejected from the ports may have a wide variety of differing angles of ejection, including directions entering under the gum line. For example, in some embodiments, the angle of ejection of the ports differs depending on the exact fluid pressure applied by the control system. A resting conformation of the port that points more upward, for example, results in a higher angle of ejection, into the user's gums, when a lower pressure of ejection is caused by a variable-pressure pump controlled by the control system. But if a higher pressure is applied, and the elastomeric components of the port are stretched more greatly, the resulting extending conformation results in a more lateral angle of pressure for the resulting flossing line.

As with device 800, device 1100 may also comprise a motorized tongue brush, or other oral cavity brush attached to and powered by the device and conforming to any surface of the user's oral cavity or throat, and also controlled by control system 1127. Also as with device 800, and more visible in the present figure, 2 sets of tooth-accepting channels are present—namely, an upper set of tooth-accepting and -cleaning channels 1145 and a lower set of tooth-accepting and -cleaning channels 1147. Each set 1145 and 1147 is generally U-shaped to match and conform with the contour of a user's two rows of teeth (in the instance of a human user). The sets can be custom-molded to the exact impression or 3-dimensional shape of each user's mouth, for example, by comprising a heat-conformable material to match a mold of the user's teeth. An inner material, on which other structural components, may be of greater rigidity and less susceptible to such a molding process, or, in some embodiments, separated from the remainder of device 1100 during custom-molding (or vice versa, with a conformable outer shell separable from the remainder of the device during molding). Other adjustments, such as brush sizes and extensions, and the addition and exact positioning of ports, may also be custom-fit onto the device, after or as part of the molding process, avoiding the dangers of heat or other chemicals facilitating molding by adding those other components to the molded components later.

Although the example of dentifrice, water and otherfluid-containing tanks has been provided, it should be understood that any suitable form of storage and conduit may, alternatively or in addition, be used. In some embodiments, only one tank, for dentifrice, toothpaste or other mouth washes, may be included, while water is simply applied to device 1100 and/or its brushes. In still other embodiments, external storage tanks, connected to device via flexible conduits, may instead be used. As yet another alternative, cartridges (not pictured), holding the fluid(s), may be inserted into device, and exchanged out when depleted, rather than having a permanent, on board storage tank(s).

Also, although the example of bristled brushes, similar to a conventional toothbrush, has been provided, it should be understood that any form of brush suitable for cleaning tooth surfaces may be used for any tooth-cleaning device set forth herein. In some embodiments, a rubberized, non-porous material, with cleaning ridges may be used. In other embodiments, ultrasound or other waves or vibrations may be used for cleaning rather than brushes. For example, even the fluid ejected from the flossing ports may include a vibrational actuator, and/or ultrasound for moving the fluid, surrounding air or other fluid ejected from the ports or surrounding the user's teeth. Preferably, a combination of more than one of each of these approaches is included, and cycled in a mode for optimally, or deep-cleaning the user's teeth.

FIG. 12 is a process flow diagram depicting exemplary steps 1200 that may taken by a control system carrying out aspects of the present invention, such as the control systems discussed above, and in reference to FIG. 10, controlling bite-actuable cleaning device 1100.

Beginning with step 1201, the control system, such as the control system set forth above in reference to FIGS. 10 and 11, first determines whether device 1100 is powered on (e.g., by a user depressing main power button 1107), meaning that the control system receiving power from a power source (e.g., a local lithium-ion battery with sufficient power to power the operations of the control system and device 1100.) If not, in some embodiments, the control system may indicate that recharging is necessary (for example, by causing its display 1113 to flash yellow). In some embodiments, the control system may next proceed to step 1203, in which it further determines whether a user has inserted his or her teeth sufficiently into the teeth-accepting channels of device 1100 before proceeding (e.g., with pressure sensors, and requiring a sufficient number and pressure within the teeth-accepting channels of the device). Next, in step 1205, the system next determines what mode the user has selected for use of the device. For example, in a regular mode, a regular or default length of time, intensity or length of brush strokes, type of brush movement or ultrasound or other vibration levels or characteristics may be selected and carried out by the control system when actuating ports, brushes and other aspects of the device. In other, more brief modes, a user may indicate that a faster clean (e.g., when no food has been consumed, in the morning) is desired, and the system will carry out a less vigorous, less lengthy, cleansing routine. In a more intense than default mode, by contrast, such as a whitening mode, the system may carry out a more vigorous, deep-cleaning and lengthy routine when carrying out the remainder of the steps set forth in this figure. As yet another example, a mode emphasizing the cleansing and massaging of the gums—for example, with the lower pressure ejection actuation discussed above—may be carried out.

However, if power has been activated and is sufficient, and regardless of the mode selected, the control system then proceeds to step 1207, in which it first implements a delay while readying the cleansing routine. Proceeding to step 1209, in some embodiments, the control system may begin to power the brushes and flossing lines of the device, but in a graduated, slowly accelerating manner. In step 1211, and as speed is slowly building, the system may pump water through the ejection ports, with an increasing amount of dentifrice, pre-rinsing the user's teeth. In some embodiments, the device also flushes water and debris in this step, potentially activating a valve to release fluid, draining it away from the device and into a storage container within the device (or into the user's sink through a release hatch). Proceeding to step 1213, the system may begin to increase the amount of dentifrice and treatment fluids, soaking the user's teeth. In steps 1215 and 1217, the system may begin to increase the cleansing activity and speed of the brushes, in stages. In step 1219, the system may begin to actuate the floss lines of the device and, in some embodiments, threading them into the user's teeth, while, in others, creating lines of fluid, as set forth in greater detail above. At any point during this routine, the system and/or the user may elect to flush the device with water, and/or pause the scrubbing activity of the flossing and brushes, in optional steps 1210 and 1212 and 1221. Finally, the control system may repeat any of these steps, before returning to the starting position, in step 1223.

I claim:

1. A dental hygiene device comprising:
a set of at least one channel(s) configured to accept each of a mammalian user's teeth;
wherein said set of at least one channel(s) comprises flossing lines configured to penetrate and pass material between teeth of said mammalian user;
a control system, comprising a power source, computer hardware and motors;
at least one brush(es) at least partially lining said channel (s), configured to be driven by said motors; and
wherein said control system is configured to activate said motors based on a user-issued command.

2. The dental hygiene device of claim 1, wherein the user-issued command comprises a user biting into said at least one channel(s), which is sensed by the control system.

3. The dental hygiene device of claim 1, wherein the user-issued command comprises a user touching a button on the outer surface of said device.

4. The dental hygiene device of claim 1, wherein the user-issued command comprises both:
a user biting into said at least one channel(s), which is sensed by the control system; and
a user touching a button on the outer surface of said device.

5. The dental hygiene device of claim 1, wherein said flossing lines comprise dental floss.

6. The dental hygiene device of claim 1, wherein said flossing lines comprise flossing projections.

7. The dental hygiene device of claim 6, wherein said flossing lines comprise ejection ports configured to eject fluid(s).

8. The dental hygiene device of claim 7, wherein said ejection ports are configured to pulse said fluids during ejection of said fluids.

9. The dental hygiene device of claim 1, wherein said dental hygiene device is configured to generate vibrations to clean a user's teeth.

10. The dental hygiene device of claim 1, wherein said dental hygiene device is configured to generate ultrasound to clean a user's teeth.

11. The dental hygiene device of claim 10, wherein said dental hygiene device is configured to be operated in a plurality of modes controlled by said control system.

12. The dental hygiene device of claim 11, wherein any of said plurality of modes may be selected by a user of said dental hygiene device.

13. The dental hygiene device of claim 1, wherein said dental hygiene device is configured to be operated in a plurality of modes controlled by said control system.

14. The dental hygiene device of claim 13, wherein any of said plurality of modes may be selected by a user of said dental hygiene device.

15. The dental hygiene device of claim 1, wherein said dental hygiene device comprises a handle.

16. The dental hygiene device of claim 15, wherein said handle is curved.

17. The dental hygiene device of claim 16, wherein said handle is crescent-shaped.

18. The dental hygiene device of claim 15, wherein said handle comprises at least one button configured to issue commands to said control system.

19. The dental hygiene device of claim 1, wherein said set of at least one channel(s) is U-shaped.

20. The dental hygiene device of claim 19, wherein said set of at least one channel(s) is custom-fitted to a user's teeth.

* * * * *